United States Patent
Huet et al.

(10) Patent No.: US 8,289,510 B2
(45) Date of Patent: Oct. 16, 2012

(54) PROCESS EXCURSION DETECTION

(75) Inventors: Patrick Y. Huet, San Jose, CA (US); Robinson Piramuthu, San Jose, CA (US); Martin Plihal, Pleasanton, CA (US); Christopher W. Lee, San Ramon, CA (US); Cho H. Teh, Cupertino, CA (US); Yan Xiong, Sunnyvale, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 72 days.

(21) Appl. No.: 13/024,471

(22) Filed: Feb. 10, 2011

(65) Prior Publication Data

US 2011/0137576 A1 Jun. 9, 2011

Related U.S. Application Data

(62) Division of application No. 12/626,021, filed on Nov. 25, 2009, now abandoned, which is a division of application No. 12/117,823, filed on May 9, 2008, now Pat. No. 7,646,476, which is a division of application No. 10/717,403, filed on Nov. 19, 2003, now Pat. No. 7,394,534.

(51) Int. Cl.
*G01N 21/00* (2006.01)

(52) U.S. Cl. .................................................. 356/237.5
(58) Field of Classification Search ........................ None
See application file for complete search history.

(56) References Cited

OTHER PUBLICATIONS

Diebold et al., Handbook of Silicon Semiconductor Metrology, SEMATECH publication, year unknown, pp. 25-30 and relevant figures.

*Primary Examiner* — Layla Lauchman
*Assistant Examiner* — Juan D Valentin, II
(74) *Attorney, Agent, or Firm* — Luedeka Neely Group, P.C.

(57) ABSTRACT

A method for analyzing defect information on a substrate, including logically dividing the substrate into zones, and detecting defects on the substrate to produce the defect information. The defect information from the substrate is analyzed on a zone by zone basis to produce defect level classifications for the defects within each zone. The zonal defect level classifications are analyzed according to at least one analysis method. The defect level classifications are preferably selected from a group of defect level classifications that is specified by a recipe. Preferably, the at least one analysis method includes at least one of zonal defect distribution, automatic defect classification, spatial signature analysis, and excursion detection. The defect level classifications preferably include at least one of individual defect, defect cluster, and spatial signature analysis signature. In one embodiment the defect information is logically divided into configurable zones after the defects on the substrate have been detected.

5 Claims, 5 Drawing Sheets

PROCESS EXCURSION DETECTION

This application is a divisional application of, and claims priority and all rights and benefits on prior pending application Ser. Nos. 12/626,021 filed Nov. 25, 2009, which was a divisional application of prior application Ser. No. 12/117,823 filed May 9, 2008, now U.S. Pat. No. 7,646,476, which was a divisional application of prior application Ser. No. 10/717,403 filed Nov. 19, 2003, now U.S. Pat. No. 7,394,534. This invention relates to the field of inspection equipment. More particularly, this invention relates to inspection equipment for the integrated circuit fabrication industry.

FIELD

Background

Modern integrated circuits, such as monolithic semiconductor devices formed on substrates of Group IV materials such as silicon or germanium, or Group III-V materials such as gallium arsenide, or combinations of such materials, are fabricated using extremely complex processes. These processes can be generally categorized into a few different groups, such as photolithographic, deposition, and etching. Process steps that fall into one or more of these different groups are applied over and over again, forming the integrated circuit layer by layer, until it is completed.

Because both the integrated circuit itself and the process by which it is formed are so complex, there are innumerable ways in which defects and flaws can creep in to the fabrication process. Such defects are able to not only degrade the ability of the integrated circuit to function properly, but can reduce its anticipated lifetime, or cause it to not function at all. These defects can be related to a myriad of different sources, such as materials issues, handling issues, and process capability issues.

Because of the great number of potential pitfalls during integrated circuit fabrication, and the extreme cost associated with the defects caused by such, it is very important to become aware of defects and identify their sources as soon as possible. In this manner, there might be some type of remedy or rework that can be timely applied to the integrated circuits that exhibit the defects, or more likely, the source of those defects can be corrected as soon as possible, so that additional integrated circuits are not impacted by the problem.

Thus, in-line inspections are an important part of the integrated circuit fabrication process. These inspections are conducted at many different points during the fabrication process, and in some instances are conducted virtually after each individual process step. In this manner, defects and their sources are hopefully detected and identified in a timely manner, before too many integrated circuits are affected.

One important classification of such inspections are optical inspections, meaning inspections that are intended to identify defects that can be seen in some manner. These optical inspections have traditionally been done manually, meaning that a human inspector looks at the substrate, typically called a wafer, on which the integrated circuits are formed. First, an inspection may be conducted with the naked eye, which hopefully detects large defects, or large patterns of defects. Next, the inspector may look at the substrate under some type of microscope to determine additional information about the nature of the defects, or to detect defects which cannot be observed by the naked eye.

Unfortunately, such manual inspection of substrates is somewhat insufficient. For example, such manual inspection is extremely tedious to perform. Thus, human inspectors tend to tire and stop noticing the more subtle defects. In addition, due to the difference in the training, experience, and ability from one inspector to the next, the data that is produced in this manner tends to be extremely difficult to integrate into a production system that can use the data to identify problems and improve processes.

For this reason, various automated optical inspection methods and analysis systems have been developed. Unfortunately, such systems tend to be very limited in their capabilities as compared to a human inspector, generally because of their more limited cognitive and associative abilities as compared to a human. Thus, such automated optical inspection and analysis systems often miss things that an experienced and careful human inspector would find.

Thus, well trained and alert human inspectors tend to recognize and identify defects better, but automated systems are less subjective and more repeatable. What is needed, therefore, are automated analysis methods that increase the ability of an automated inspection and analysis system to recognize the sources of defects.

SUMMARY

The above and other needs are met by a method for analyzing defect information on a substrate, including logically dividing the substrate into zones, and detecting defects on the substrate to produce the defect information. The defect information from the substrate is analyzed on a zone by zone basis to produce defect level classifications for the defects within each zone. The zonal defect level classifications are analyzed according to at least one analysis method. The defect level classifications are preferably selected from a group of defect level classifications that is specified by a recipe. Preferably, the at least one analysis method includes at least one of zonal defect distribution, automatic defect classification, spatial signature analysis, and excursion detection. The defect level classifications preferably include at least one of individual defect, defect cluster, and spatial signature analysis signature. In one embodiment the defect information is logically divided into configurable zones after the defects on the substrate have been detected.

According to another aspect of the invention there is described a method for detecting process excursions from defect information from a substrate, including analyzing the defect information based on a list of selectable factors to determine spatial signature analysis signatures. A process problem identification is selectively assigned to the substrate based on a combination of more than one spatial signature analysis signatures detected on the substrate. The list of selectable factors preferably includes at least one of a number of events, an average density of an event, a number of die affected, an effective length of event, an area covered by event, and a location of event relative to substrate center.

Preferably, the step of selectively assigning the process problem identification is accomplished with a table that includes a numeric process problem identification, a string process problem identification, a Boolean expression of component spatial signature analysis signatures, a remedial action, a notification action, a layer identification, and a severity level. The step of selectively assigning a process problem identification to the substrate most preferably includes assigning a substrate identification to the substrate and storing the substrate identification and the process problem identification in a database. Preferably, more than one process problem identification can be assigned to each substrate.

According to still another aspect of the invention there is described a method for detecting process excursions, including detecting defects on a selectable set of substrates. The defects detected on the set of substrates are composited into an effectual substrate defect set. The effectual substrate defect set is analyzed with a spatial analysis routine. The spatial analysis routine preferably includes at least one of spatial signature analysis and repeater analysis. In various embodiments, the selectable set of substrates includes substrates that all belong to a given lot, or every nth substrate from a given data set, where n is an integer that is greater than one. The step of compositing the defects into an effectual substrate defect set preferably includes at least one of translating and rotating a data set from a given substrate as needed to align with data sets from other substrates.

According to yet another aspect of the invention there is described a method for classifying defects on a substrate, including analyzing the defects with a first analysis routine that is adapted to classify larger patterns of defects, and analyzing the defects that were not classified with the first analysis routine with a second analysis routine that is adapted to classify smaller defects, using output from the first analysis routine as input to the second analysis routine. Preferably, the first analysis routine is spatial signature analysis, the second analysis routine is automated defect classification, and the output from the first analysis routine includes bounding boxes from the spatial signature analysis.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
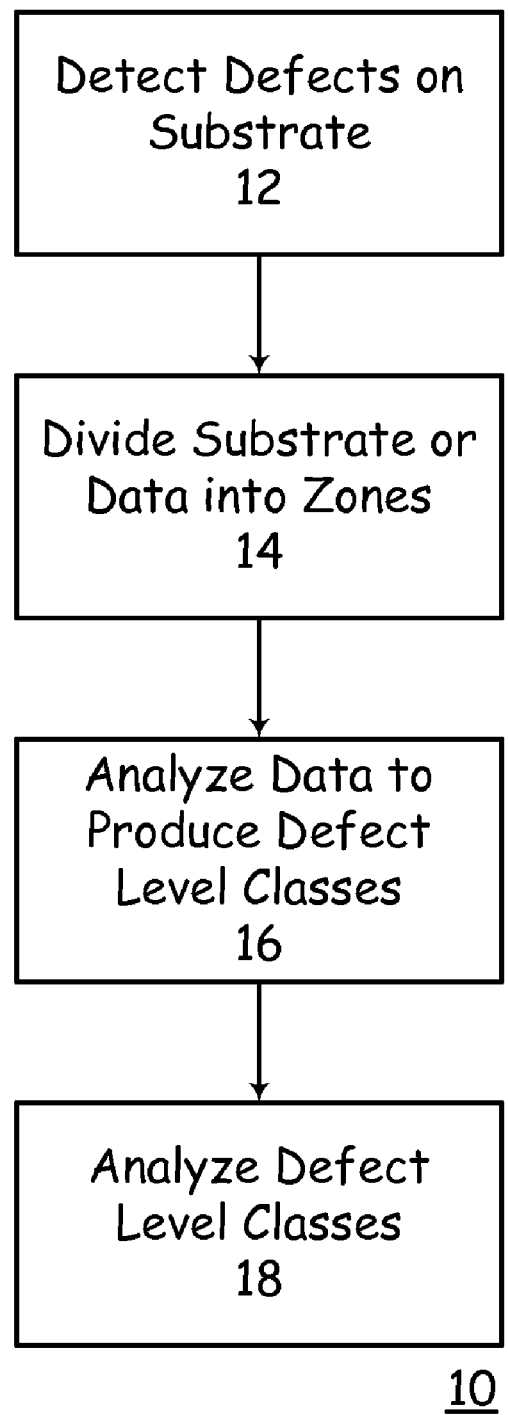
FIG. 1 is a flow chart of a method of zonal analysis according to the present invention.

This disclosure presents four methods that can be used individually or in combination with one another to enhance the identification of defects and their sources during automated inspection and analysis processes. These various methods can be implemented in a variety of ways. For example, these methods can be implemented in stand-alone optical inspection tools, or as modules that are called by an analysis routine, whether that routine be based in an adaptable, programmable inspection tool or remotely from the inspection tool, or as stand alone routines that may be invoked as desired on a data set that is input or otherwise identified by the user.

Most preferably, these methods are implemented as software routines that run on a computing platform, such as a standard personal computer type platform, as might be adapted to control the operation of and receive data from an automated optical inspection tool. Thus, in various embodiments, these methods take the form of either hardware or software, or a combination of the two. For example, embodiments of the present methods can be sold to end users as software routines on computer readable media, such as diskettes or compact disks. Alternately, embodiments can take the form of firmware upgrades to be installed in existing inspection tools. Thus, the descriptions of the various embodiments herein, which are mostly described in terms of methods, are not to be limited to method steps alone, but also to physical embodiments of those methods.

These methods are primarily concerned with the analysis of data that has already been generated, such as data that is generated by the optical inspection of a substrate, where the data represents the properties of defects that have been detected, such as location, shape, and size. However, in alternate embodiments, the data could conceivably be generated in some other manner. Further, the primary purpose of the methods described below is to determine in a timely manner whether a deleterious and correctable event has occurred, such as a process excursion, so that the event can be corrected before additional substrates are misprocessed or otherwise damaged. However, in other embodiments the data is analyzed for other purposes, such as for general process improvement.

Zonal Defect Level Classification

Various problems that occur during substrate processing frequently leave characteristic signatures on the substrate, in the form of optically detectable defect distributions. For example, one type of signature is a ring, which might be perceptible to the naked eye. However, the ring—which is the signature—is actually formed not of a single, continuous defect, but of a series of smaller defects. Recognizing the signature from an analysis of the pattern of the individual defects is called spatial signature analysis. If spatial signature analysis is not performed, it is likely that one will miss the forest for the tress, so to speak. In many cases, such signature defect distributions are traceable to a particular process problem, and also appear in specific and repeatable locations on the substrate from one occurrence to another.

To perform zonal analysis, the defects on the substrate are detected, as given in block 12 of FIG. 1. Either the substrate itself or the defect data is logically divided into several zones of interest as given in block 14, and defects are binned according to the zones in which they are found. One of the disadvantages of prior art methods of zonal analysis is that they are extremely inflexible. They can only analyze substrate zones for certain event level properties, such as the number of defects and the density of the defects in each zone. Thus, they are particularly unsuitable for an integrated analysis that uses additional analysis techniques. For example, because these event level properties are divided into zones, they tend to be in a form that is difficult, if not impossible, to use in spatial signature analysis, or other advanced cognitive analyses.

According to the present invention, zonal analysis is recipe driven, in that all aspects of the zonal analysis relevant to the user are configurable through a recipe. Preferably, the zonal analysis works on arbitrary defect distributions specified by a list of attributes. For example, the zonal analysis can be performed with individual defects, defect clusters, spatial signature analysis signatures, and so forth in mind.

Thus, rather than producing event level classifications like the prior art methods of zonal analysis, the present method generates defect level classifications as given in block 16, using the recipe instructions input by the user, or entered from a central database. Various class identifications are preferably assigned to each of the defects in the input distribution. For example, these class identifications can identify classes such as clusters, spatial signature analysis signatures, and so forth.

One of the significant differences between the preferred method according to the present invention and existing zonal analyses is that the latter are limited to identifying zonal membership for individual events, such as defects, defective pixels, defective dies, and so forth. However, the method described herein preferably classifies individual events into visually recognizable patterns of events, such as a spatial signature, as a first step. Each recognized pattern, rather than just individual events, is then subsequently treated as a single entity during a zonal analysis. Users preferably configure a list of patterns that are of interest to them, and also a list of zones that are of interest to them. Most preferably, the patterns in the one list are associated with the zones in the other list, based on a relationship between them as determined by previously identified process problems.

For example, users may wish to identify long straight scratches or other such events (the pattern of interest) near the wafer notch (the location of interest), because they know that the relationship between this pattern and this location indicates an identifiable process problem, which is preferably automatically brought to the user's attention by the system when the relationship is detected in the data. The user may decide to not set a specific relationship for long straight scratches in other locations on the substrate, preferring instead to just be made aware of such, without being notified of any predetermined relationship. Alternately, the user may set up several such relationships, depending at least in part upon where on the substrate the pattern of interest is located.

Thus, zonal analysis is performed on patterns of interest treated as determined by the user recipe. If a signature falls into a zone of interest, the signature is preferably reclassified according to the user recipe. The resulting classification provides much more accurate information for identification of certain types of process problems. It allows the user to readily distinguish between two causes that leave spatially identical signatures on the substrate, but which are located at different characteristic zones on the substrate.

On the other hand, existing zonal analyses merely separate events into zones and determine certain properties of the zones, such as the number and density of events in each zone. However, they do not tie together this information with either the spatial pattern of event clusters or any other attribute of the event.

Thus, the preferred methods according to the present invention provide a more flexible analysis targeted at spatially correlated events of interest. The result of the analysis is a reclassification of the whole pattern into a new class that carries information not only about the spatial pattern but also about its spatial context on the substrate. The existing methods only determine membership of individual events to substrate zones and calculate simple properties of the zones based on the result, such as the number of events per zone. However, calculation of these properties is easily available in the present method as well.

It is noted that the target for zonal analysis in the present invention does not necessarily need to be a spatial pattern. It can be a cluster of events based on any other event level attribute, such as repeater or cluster identification. Further, the word "event" as used herein includes several concepts, including defect, defective pixels, defective die, or any other spatially definable event on the substrate.

Figure 5:
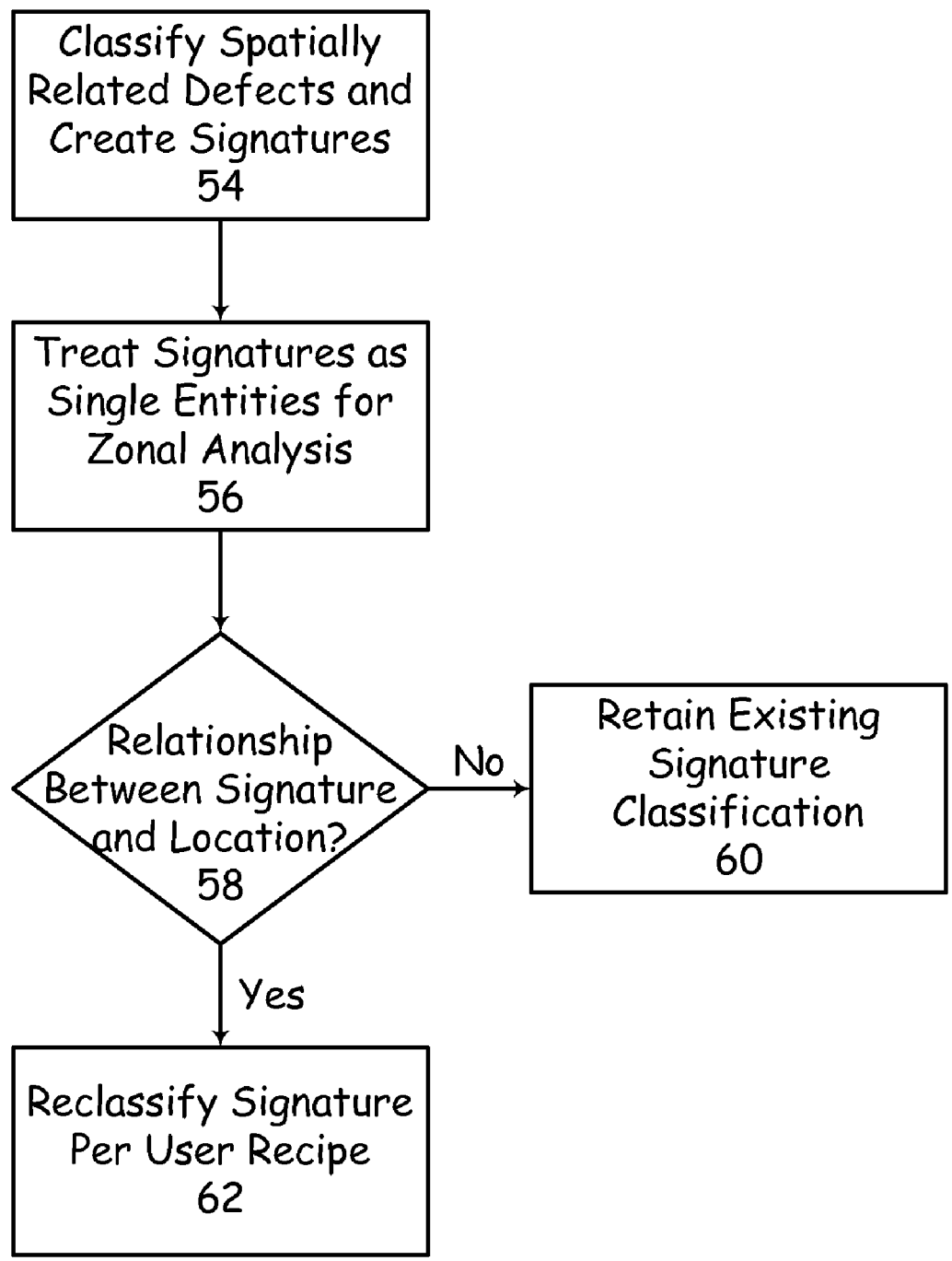
FIG. 5 is a flow chart of a method of using spatial signature analysis in zonal analysis according to the present invention.

FIG. 5 is a more detailed flow chart of the process flow 52 according to the present invention. As mentioned above, the detected defects are analyzed, and classifications are preferably generated for spatially related defects, as given in block 54. In addition, higher level objects are preferably created, consisting of spatial signatures of particular shape. Each of the signatures generated in that step are then preferably treated as a single entity for the sake of zonal analysis, as given in block 56. It is noted that the preferred method also analyzes the individual defects during zonal analysis, in addition to the signatures. If the signature of a particular type falls into a particular zone of interest on the substrate, as identified by the user such as through a recipe, then the process branches as given in block 58. When a relationship is found, the entire signature of defects is reclassified according to the user's recipe, as given in block 62. If a relationship is not found, then the existing classification of the signature is retained.

Because this zonal analysis produces defect level classifications only, and not the event level classifications of prior art systems, this analysis is not limited to any specific intended application, such as the mere binning of the number of defects and the density of defects. Instead, the present method allows any attribute based analysis to follow, as given in block 18 of FIG. 1. For example, defect density or defect count can be calculated for each zone, as was previously possible, however, a new classification can be used for excursion detection, for example. Thus, prior art zonal analyses provide only a subset of the capabilities of the new method.

Multi-Factor Spatial Signature Analysis

Detection of problems such as process excursions is typically based on information such as total defect count of signatures, total number of signatures of a particular type (such as a scratch), and detection of a particular type of signature (such as a ring). However, current methods do not identify process problems based on combinations of information from different types of detected signatures, whereas the method described herein looks at combinations of signatures to identify processing problems.

For example, detection of a single signature such as ring may indicate one process problem or excursion, whereas detection of the same ring in combination with heavy vertical lines may indicate a completely different process excursion. The first condition may not be harmful, whereas the second condition may require immediate attention to reduce future yield losses. Therefore, looking at combinations of detected signatures tends to provide information that is more valuable than looking at isolated signature data, and increases the ability of the method to differentiate one process problem from another For example, the signature information that can be used in this method includes the number of defects, the average density of the defects, the number of dice on the substrate effected by the defects, the effective length of the defects, the area over which the defects are scattered, and the location of the defects, such as with respect to the center of the substrate. By looking at combinations of such information, rather than at isolated events, a greater amount of process information can be deduced.

Figure 2:
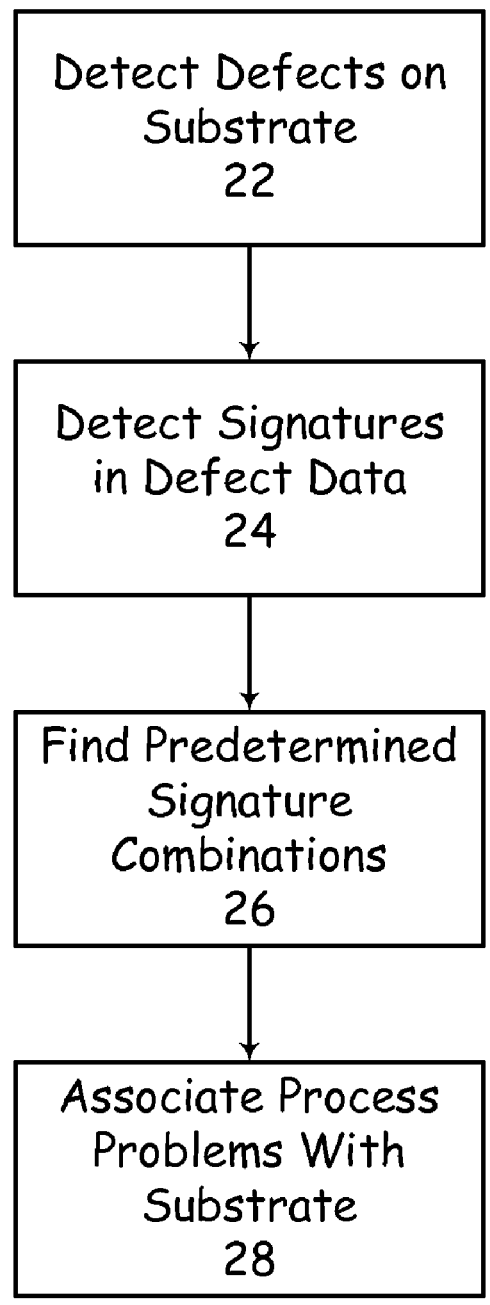
FIG. 2 is a flow chart of a method of determining process excursions based on combinations of spatial signature analysis signatures according to the present invention.

For example, in one embodiment, the defects on the substrate are detected, as given in block 22 of FIG. 2. The various signatures inherent in the defect data are then detected, as given in block 24. Predetermined combinations of signatures are next found, as given in block 26, which predetermined combinations indicate various process problems. Each process problem is assigned an identification, and the signatures associated with the process problem are identified. When that combination of signatures is detected, an identification is assigned to the inspected substrate that exhibits the detected condition, and this information is stored in a database of some type, such as for future reference, as given in block 28. Preferably, multiple identifications can be assigned to each substrate, based on the signature combinations that are found on the substrate. For example, there may be more than one process with a problem at a given time, the effects of which can be optically identified on the substrate.

This method can be implemented such as in a table that is interrogated during an analysis, where each row includes information in regard to a particular process problem. For example, the table may include information such as a numeric and string identification for the problem, a Boolean or other expression of the signature combination that identifies that problem, a description of remedial or reporting actions to be taken when the problem is identified, and an identification of the relative severity of the problem. In addition, the table may include an identification of the layer on which the problem occurs, such as a planarized layer, a lithographic layer, an etched layer, a deposited layer, and so forth. This may be important, because a ring signature may have a different interpretation on a planarized layer than it does on a lithographic layer, for example.

Spatial Substrate Stacking

Spatial analysis operates on information that is typically extracted from a single substrate that underwent a particular process or tool manipulation. The success of the spatial analysis, such as signature analysis or repeater analysis, tends to rely on whether the single substrate from which the data is collected is sufficiently impacted by the process or tool excursion, such that the substrate receives a sufficient number of spatial characteristics, and spatial characteristics of a sufficient intensity, such that the spatial characteristics rise above the noise level of other optically detectable events on the substrate. Since these conditions are not always met, substrate level spatial analysis may leave a growing critical process excursion undetected until it causes serious damage to the yield of the process or tool.

Figure 3:
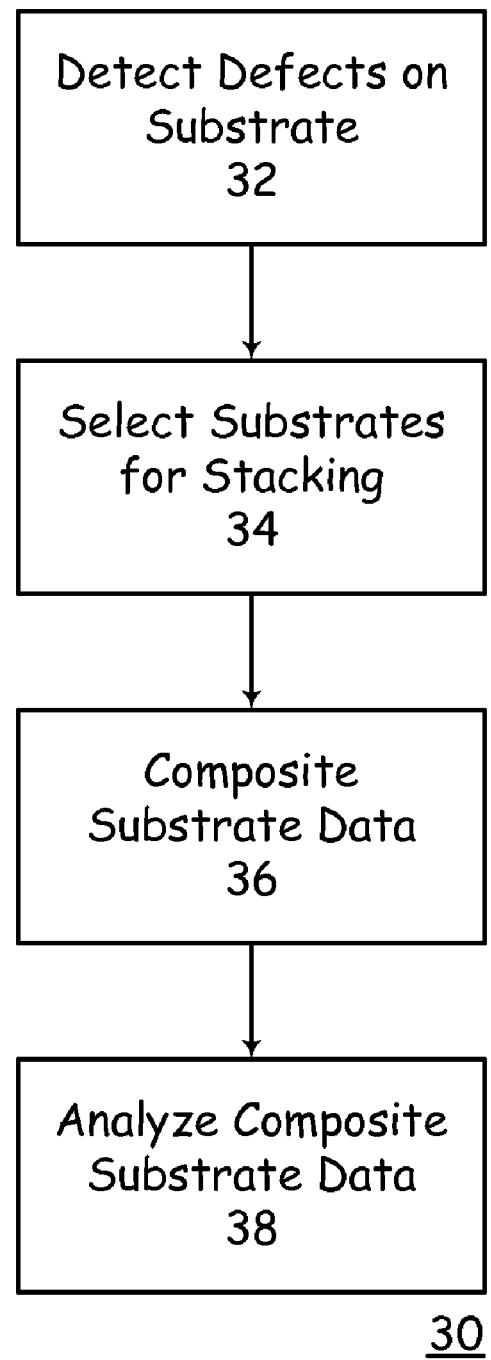
FIG. 3 is a flow chart of a method of spatial wafer stacking according to the present invention.

To detect these critical but hard to find excursions, spatial signature analysis is preferably performed on defect data that is accumulated from many different substrates, as given in block 32 of FIG. 3, that all have the same or similar process history. Preferably, a mechanism is used to select for stacking the data from many different substrates with a common processing history, as given in block 34. The data selection process preferably includes correlating defect data with work in progress information, and is preferably user configurable. The work in progress data includes the common process history information for the substrates. Thus, the work in progress data includes information such as, for example, which substrates were processed in a given chamber. By stacking the substrate information in such a manner, process departures for a given process history can be more easily detected.

For example, the selection process may include a single substrate (meaning no stacking), an entire lot of substrates, an entire data set as determined by something other than lot, every $n^{th}$ inspected substrate in the data set, or some other sampling mechanism as desired, and a previously computed split attribute, such as by process tool or process chamber.

The spatial information contained within the different substrates that are selected as given above is preferably combined for the analysis, as given in block 36. This process preferably includes creating an effectual set of composite data that looks like it came from a single substrate, so that it can be processed by any spatial analysis routine, such as spatial signature analysis or repeater analysis, as given in block 38. The effectual substrate data is referred to herein as the "substrate stack." Preferably, the method wherein the substrate stack is created takes into account various possible differences in the data sets for individual substrates, such as data translation, rotation, and scaling misalignments that are a result of variations between different pieces of inspection equipment, temperature variations, alignment variations, and so forth.

Spatial substrate stacking thus enhances the ability of the analysis routine to provide an early detection of process excursions that do not leave a pronounced signature on a substrate, at least not initially. Substrate stacking can be integrated into various systems, such as an inspection tool analysis engine, where it is invoked as a part of a runtime inspection sequence. For example, the method can be used to stack a selected subset of substrate data at the end of each lot of substrates that is inspected by the tool, and then used to report the results through the tool connection to the management engineering system, which is preferably configured to trigger on such an excursion.

Alternately, the method can be implemented in a load time analysis engine, and invoked from a lot based event. This allows stacking on data from many different inspection tools and from inspection tools made by different manufacturers. Further yet, the method can be implemented in an engineering data analysis engine, which thereby allows the greatest flexibility in selecting data from a large defect and work in progress database.

Hierarchical Defect Classification

Substrate defects range in size from big defects of a few centimeters in size, to small defects having a size on the order of the thickness of a human hair. For example, on a typical three hundred millimeter diameter substrate, defects range from the global signature of a big circular ring defect covering the substrate edge boundary, to a small particle that may be only twenty-five microns in diameter. Hierarchical classification uses an ordered selection of analysis methods, such as spatial signature analysis and automatic defect classification, to classify the defects, thereby providing the ability to automatically classify substrate defects of various sizes in a semiconductor substrate process.

Figure 4:
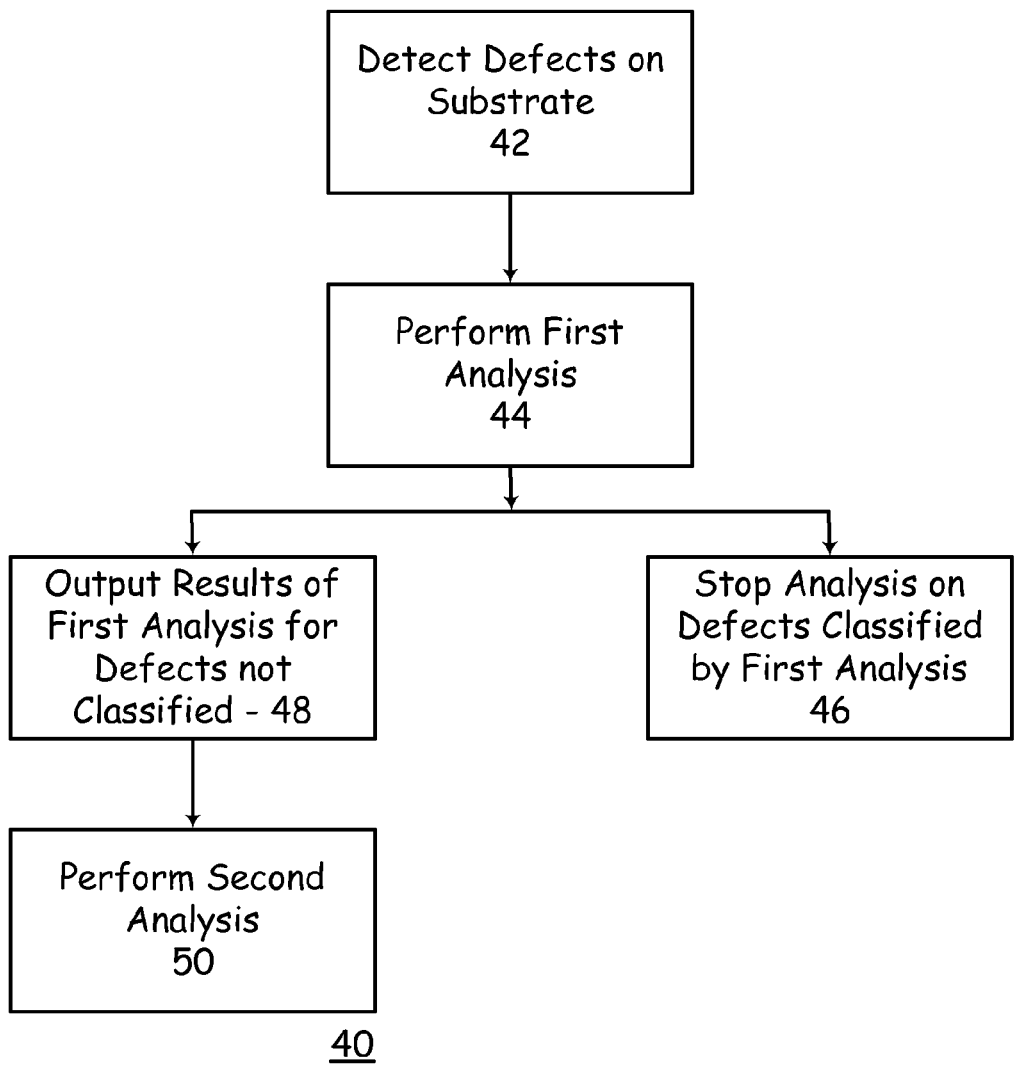
FIG. 4 is a flow chart of a method of hierarchical classification of defects according to the present invention.

The hierarchical classification method described herein automatically classifies substrate defects using a multi-stepped approach, such as a two step approach, which is implemented after the defects are detected, as given in block 42 of FIG. 4. The first step is to automatically analyze the defects using the first analysis method as given in block 44, which is preferably spatial signature analysis, which is useful to classify larger defects into a set of defined signatures, as given in block 46. The second step is to use the detailed spatial signature analysis results including the bounding boxes, of those small localized defects that did not produce spatial signature analysis signatures, as given in block 48, to further analyze their gray level images and automatically classify the small defects into a set of defined defect classes, preferably using automated defect classification, as given in block 50.

The preferred flow of the inspection post-processing is as follows. The inspection tool preferably generates an image of the substrate. The defects on the substrate, represented by "defective" pixels in the image, are identified by one or more of a number of different thresholding methods, and the defects are converted into points on the substrate. Most preferably, this includes identification of a bounding box size. Spatial signature analysis of the entire substrate, or at least of the inspected area of the substrate, is then performed on this data, which is preferably the collection of points representing thresholded defective pixels.

The result of the spatial analysis is two-fold. First, spatially recognizable patterns of defects are classified by the spatial signature analysis. Second, the rest of the defects are either random events or belong to spatial clusters whose shape is not recognizable by the spatial signature analysis with sufficient accuracy or confidence. In the latter case, spatial signature analysis still provides useful information by providing the bounding box around the clusters of spatially correlated defects to indicate to the subsequent automatic defect classification scheme what to classify, i.e. what are the patch images. Finally, the automatic defect classification routine receives an image for each bounding box supplied by the spatial signature analysis, and performs detailed classification using the full image information.

This automatic hierarchical classification method enables the quick detection of yield related process problems, and implementation of corrective action into the processes in a timely manner, which speeds up root cause analysis in yield process management and reduces the cost of substrate rework. The opportunities for savings are expected to be greater on shrinking technologies having higher substrate and die costs.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A processor-based method for classifying defects on a substrate, the method comprising the steps of:
    using a processor, analyzing the defects with a first analysis routine to classify larger patterns of defects, and
    using the processor, analyzing the defects that were not classified with the first analysis routine with a second analysis routine to classify smaller defects, using output from the first analysis routine as input to the second analysis routine.

2. The method of claim 1, wherein the first analysis routine is spatial signature analysis.

3. The method of claim 1, wherein the second analysis routine is automated defect classification.

4. The method of claim 1, wherein the output from the first analysis routine includes bounding boxes from a spatial signature analysis.

5. The method of claim 1, wherein the first analysis routine is spatial signature analysis and the second analysis routine is automated defect classification, and the output from the first analysis routine includes bounding boxes.

* * * * *